United States Patent [19]

Zielke

[11] Patent Number: 4,854,304

[45] Date of Patent: Aug. 8, 1989

[54] IMPLANT FOR THE OPERATIVE CORRECTION OF SPINAL DEFORMITY

[75] Inventor: Klaus Zielke, Bad Wildungen, Fed. Rep. of Germany

[73] Assignee: Oscobal AG, Selzach, Switzerland

[21] Appl. No.: 168,514

[22] Filed: Mar. 15, 1988

[30] Foreign Application Priority Data

Mar. 19, 1987 [DE] Fed. Rep. of Germany ... 8704134[U]

[51] Int. Cl.$^4$ .......................... A61F 5/00; A61B 17/00
[52] U.S. Cl. ............................... 128/69; 128/92 YM; 623/17
[58] Field of Search ................. 623/17; 128/69, 92 Z, 128/92 ZZ, 92 YZ, 92 YK, 92 ZW, 92 YM, 92 YF, 92 YE

[56] References Cited

U.S. PATENT DOCUMENTS

| | | | |
|---|---|---|---|
| 4,274,401 | 6/1981 | Miskew | 128/92 YM X |
| 4,361,141 | 11/1982 | Tanner | 128/92 YM X |
| 4,422,451 | 12/1983 | Kalamchi | 128/92 YM X |
| 4,567,884 | 2/1986 | Edwards | 129/92 YM X |

FOREIGN PATENT DOCUMENTS 3306657 9/1984 Fed. Rep. of Germany .

OTHER PUBLICATIONS

Downs Surgical, "Spinal Surgery Instrumentation", published at least by 1976, possibly earlier.
Edwards, "Spinal Fixation System", published at least by 1982, possibly earlier.
Ulrich, "Ventrale Derotations Spondylodese", published at least by 1969, possibly earlier.

Primary Examiner—Richard J. Apley
Assistant Examiner—David J. Bender
Attorney, Agent, or Firm—Marks Murase & White

[57] ABSTRACT

An implant for the operative correction of spinal deformity, in particular scoliosis, kyphosis, and lordosis, which is a distraction and compression rod, having at one of its end a ratchet part formed by circumferential saw notches conically broadening toward the top and ending in a flat surface for receiving spinal hooks, a cylindrical part followed by a threaded part, the threaded part being build for receiving the heads of bone screws fixed by nuts, wherein the ratchet part of the rod is used for distraction and the threaded part of the rod is used for compression as well as distraction of the deformed spine.

2 Claims, 1 Drawing Sheet

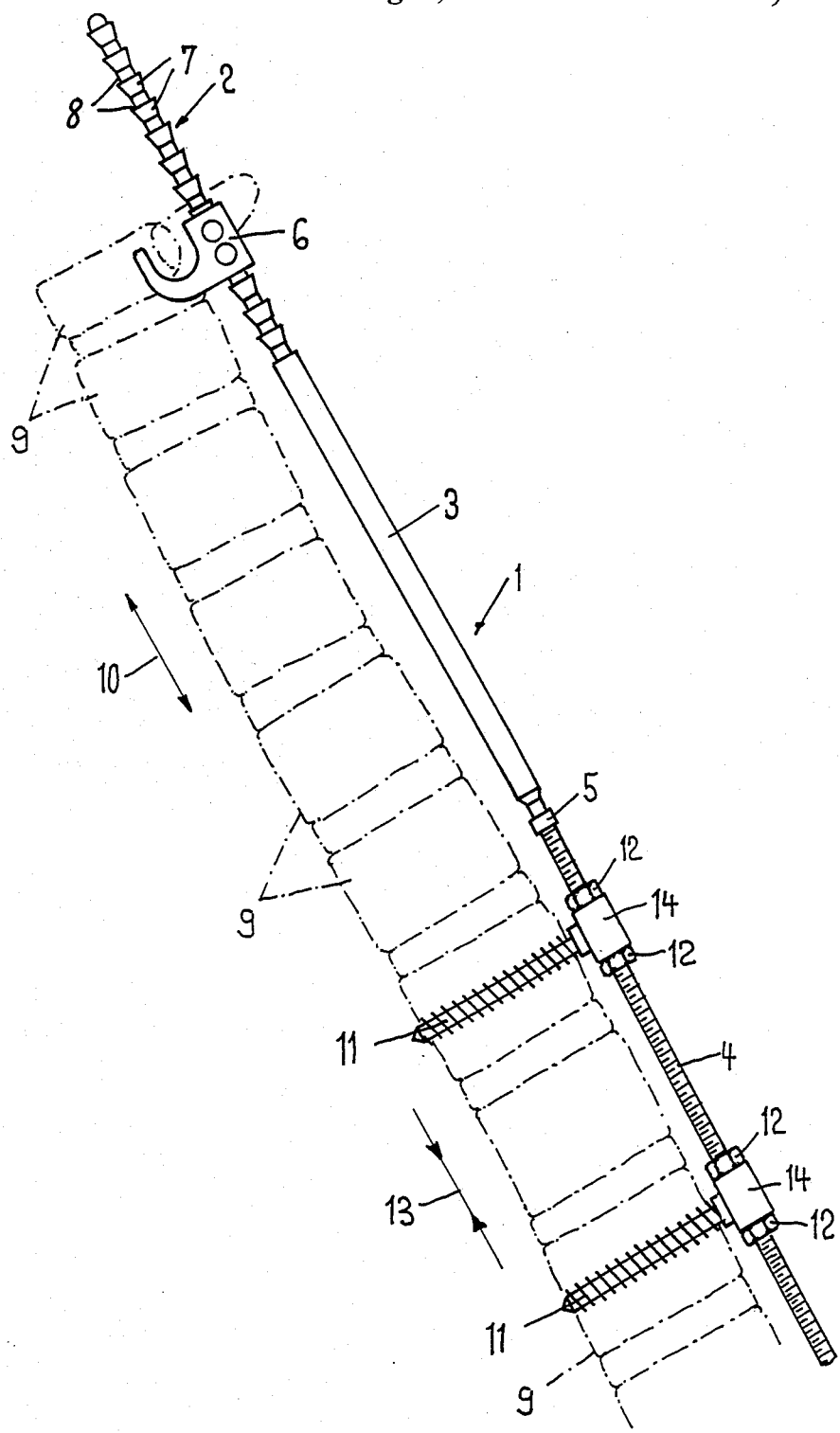

IMPLANT FOR THE OPERATIVE CORRECTION OF SPINAL DEFORMITY

BACKGROUND OF THE INVENTION

The present invention refers to an implant for the operative correction of spinal deformity, such as scoliosis, kyphosis, and lordosis from the rear access.

Since 1962 the HARRINGTON distraction rod is known, comprising at its upper end a multitude of saw notches which are able to receive a hook and which are formed thus that a force between the hook and the rod can only be applied in one direction, in the direction of distraction. At the lower end of the rod there is a collar serving as stop for a fixed hook. For correcting a spinal deformity two hooks are arranged at the distraction rod, on both sides of the deformity, whereby the lower hook is fixed and the upper hook is displaced thus that the desired correction of the deformity of the spine is effectuated.

Since 1961 the HARRINGTON compression rod is also known. It comprises a thread along its entire length for receiving nuts. With the aid of the nuts hooks, running by a bore on the rod, can be displaced. They are fastened on the convex side of the deformity. They are displaced against each other, thus shortening the convex side, resulting in a supplemental correction of the deformity.

The two HARRINGTON rods form a system exercising distraction and compression forces for the correction of a spinal deformity from the rear.

A correction implant for the ventral derotation spondylodese (known as V.D.S.) is further known, consisting of a compression rod with thread, on which nuts are displaceable. Those nuts fit with a cylindrical part in a recess in bone screws. By displacing the bone screws on the threaded rod the convexity of a deformity can be reduced. This V.D.S. system is predominantly suited for the ventral access. If it is employed dorsal transpedicular, that is through the arch root, it must be used bilateral, that is on both sides of the spine.

SUMMARY OF THE INVENTION

It is the object of the present invention to disclose an implant for the operative correction of in particular the rear end of spinal deformity, with which it is possible to exert distraction forces as well as compression forces.

Further objects and advantages of the invention will be apparent from the following description, taken in connection with the accompanying drawing.

BRIEF DESCRIPTION OF THE DRAWING

The unique FIGURE shows schematically an implant according to the invention, in the implanted position.

DESCRIPTION OF THE PREFERRED EMBODIMENT

The FIGURE shows the distraction and compression rod 1, comprising an upper ratchet part 2 for the distraction, followed by a cylindrical middle part 3 and a threaded part 4. At the junction between the cylindrical and threaded part there is a collar 5. The circumferential saw notches 7 of the ratchet part 2 are conically broadening toward the top and are ending in a flat surface 8, so that only unidirectional forces can be received when a hook 6 is displaced along the rod.

In this figure, only one of two or more hooks 6 is shown, between which the distraction can be effectuated. The hooks are known per se and can be for example of the EDWARDS type, or as shown in the German Pat. No. 3'306 '657. The hook 6 is introduced according to a known technic between two vertebrae 9, which are schematically shown in the figure. Arrows 10 indicate the distraction.

The diameter of the cylindrical part 3 of the rod is less than the diameter of the ratchet part 2.

On the threaded part 4 several bone screws 11, fastened at its head 14 with nuts 12, can be fixed, whereby only two of them are shown. The bone screws with heads are also known per se, as well as the different systems, mostly with degrees of freedom between the rod and the screw, for fixing the screw to the rod. Each screw is fixed into one vertebra, and with the aid of the nuts it is possible to compress the vertebrae, as indicated by the arrows 13. The first nut from above can eventually be replaced by the collar 5. It is of course also possible to distract the vertebrae with the same system of bone screws and nuts.

With the aid of the distraction and compression rod according to the invention it is possible to alter the above mentioned V.D.S method thus that a connection of segmental "transpedicular" applied screws through the arch root for the compression of vertebral segments with a simultaneous possibility of distraction can be obtained. In such way a selective multisegmental influence by the same rod is given, at least at its lower end. With the aid of the upper part of the rod distracting forces can be applied, and this only in connection with the compressing correcting segmentally acting forces at the lower end of the rod. Whilst a correction by elongation of the necessary stiffening region at the upper part can be obtained, this applies by shortening in the lower part.

It follows that the dorsal, transpedicular application for distraction and compression corrections is possible with one rod. As described before, a wealth of different hooks and screw systems can be used with a rod according to the invention.

What I claim:

1. An implant for the operative correction of spinal deformity, in particular scoliosis, kyphosis, and lordosis, comprising a rod, said rod having at one of its end a ratchet part formed by circumferential saw notches conically broadening toward the top and ending in a flat surface for receiving spinal hooks, a cylindrical part followed by a threaded part, said threaded part being built for receiving the heads of bone screws fixed by nuts, wherein said ratchet part of the rod is used for distraction and said threaded part of the rod is used for compression as well as distraction of the deformed spine.

2. An implant according to claim 1, wherein said rod has a collar arranged between said cylindrical part and said threaded part.

* * * * *